United States Patent
Tonami

(10) Patent No.: US 8,411,823 B2
(45) Date of Patent: Apr. 2, 2013

(54) RADIATION GRID AND RADIOGRAPHIC APPARATUS PROVIDED WITH THE SAME

(75) Inventor: Hiromichi Tonami, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 250 days.

(21) Appl. No.: 13/056,643

(22) PCT Filed: Aug. 11, 2008

(86) PCT No.: PCT/JP2008/064428
§ 371 (c)(1),
(2), (4) Date: Jan. 28, 2011

(87) PCT Pub. No.: WO2010/018617
PCT Pub. Date: Feb. 18, 2010

(65) Prior Publication Data
US 2011/0164727 A1    Jul. 7, 2011

(51) Int. Cl.
*G01N 23/04* (2006.01)
*G21K 1/00* (2006.01)

(52) U.S. Cl. .................. 378/154; 378/62; 250/505.1

(58) Field of Classification Search ............. 378/62, 378/147, 154, 155; 250/505.1
See application file for complete search history.

(56) References Cited

U.S. PATENT DOCUMENTS

| | | | | |
|---|---|---|---|---|
| 4,340,818 A | * | 7/1982 | Barnes .................. | 378/155 |
| 5,606,589 A | * | 2/1997 | Pellegrino et al. ...... | 378/154 |
| 5,970,118 A | * | 10/1999 | Sokolov ................ | 378/155 |
| 6,438,210 B1 | * | 8/2002 | Castleberry ........... | 378/154 |
| 6,625,253 B1 | * | 9/2003 | Barnes et al. .......... | 378/155 |
| 7,072,446 B2 | | 7/2006 | Dobbs et al. | |

* cited by examiner

*Primary Examiner* — Irakli Kiknadze
(74) *Attorney, Agent, or Firm* — Cheng Law Group, PLLC

(57) ABSTRACT

This invention has an object to provide an X-ray grid without obstructing travel of direct X-rays by arranging regularly absorbing foil strips having a maintained linear shape. The X-ray grid of this invention has an absorber. The absorber maintains its shape through integration with the first seat cover via the first joining member. Moreover, the X-ray grid of this invention has sufficient strength. That is because the first joining member has a thickness larger at both ends thereof in the x-direction than the center portion between the both ends.

8 Claims, 16 Drawing Sheets

Fig.19
(a)
(b)

RADIATION GRID AND RADIOGRAPHIC APPARATUS PROVIDED WITH THE SAME

TECHNICAL FIELD

This invention relates to a radiation grid for removing scattered radiation. More particularly, this invention relates to a radiation air grid having no need for a spacer in a gap between absorbing foil strips adjacent to each other.

BACKGROUND ART

Examples of radiographic apparatus that obtain fluoroscopic images of a subject includes one in which a radiation source irradiates the subject with radiation beams in a cone shape, and a flat panel detector (hereinafter, abbreviated as "FPD") detects radiation that transmits through the subject. In such radiographic apparatus, scattered radiation occurs that scatters inside the subject in transmitting therethrough and enters into the FPD, which leads to a lower contrast fluoroscopic image of the subject, in order to prevent scattered radiation from entering into the FPD, a radiation grid may be provided that covers a radiation detection surface of the FPD.

Now, description will be given of a construction of a conventional radiation grid. As shown in FIG. 20, the conventional radiation grid 71 includes strip absorbing foil strips 72 composed of a molybdenum alloy etc., that readily absorb radiation, and spacers 73 that support them and maintain its linear shape. The absorbing foil strips 72 and spacers 73 are arranged alternately to form a plate absorber. In the radiation grid 71, direct radiation traveling through the subject passes through the gap 72 between the adjacent absorbing foil strips 72 (spacer 73, to be exact), whereas scattered radiation enters into the absorbing foil strips 72, where it is absorbed.

For obtaining clearer fluoroscopic images, it is desirable not to provide the spacers 73 that obstruct travel of direct radiation. Accordingly, a radiation air grid has been developed having no spacer 73 in recent years (see, for example, Patent Literature 1.) Here, description will be given of a construction of a conventional radiation air grid. As shown in FIG. 21, the conventional radiation air grid 81 has a pair of seat covers 85, 86 that covers an absorber 84. The radiation air grid 81 has no spacer. Thus, each of absorbing foil strips 82 is fixed through adhesion to the seat covers 85, 86.

However, only the seat covers 85, 86 cannot sufficiently support the absorbing foil strips 72. Accordingly, the absorber 84 is mechanically brittle. Consequently, in the conventional radiation air grid, the adhesive 87 penetrates side ends of the absorber 84, thereby enhancing mechanical strength of the absorber 84. For manufacture of such radiation air grid 81, two or more absorbing foil strips 82 are arranged parallel to one another. The adhesive 87 is applied so as to cover each end of the absorbing foil strips while a tension is applied to each of them, whereby the adhesive 87 penetrates the gaps between the adjacent absorbing foil strips 82. Upon curing of the adhesive 87, the seat covers 85, 86 having the adhesive 87 applied thereto cover the absorber 84, and the absorbing foil strips 82 are cut off at both ends thereof to have an even length. Accordingly, the radiation air grid 81 is to be manufactured.

[Patent Literature 1] U.S. Pat. No. 7,072,446

DISCLOSURE OF THE INVENTION

Summary of the Invention

The conventional construction, however, has the following problem. Specifically, the problem is that the conventional construction has difficulty in making the absorbing foil strips linear. Curing strain will occur during curing the adhesive 87 that penetrates the gaps between the absorption foil strips 82. Accordingly, even when the absorbing foil strips 82 are arranged parallel, the absorbing foil strips 82 gradually deviate in position due to the curing strain as the adhesive 87 cures. Finally, arrangement of the absorbing foil strips 82 varies due to the curing strain. Consequently, release of tension applied to the absorbing foil strips 82 may leads to serpentine absorbing foil strips 82 or deformed absorbing foil strips 84 into a J-shape.

Such radiation air grid is provided in the fluoroscopic apparatus, and the absorbing foil strips 82 also obstruct travel of the direct radiation, which causes streaky shadows on a fluoroscopic image. That is because strain in the absorbing foil strips 82 causes a wider shadow to be projected on the FPD. Consequently, the absorbing foil strips 82 need to be arranged linearly and regularly for obtaining a clearer fluoroscopic image.

On the other hand, it is difficult to avoid the curing strain with a small amount of the adhesive 87 to be applied in manufacture of the radiation air grid. A small amount of the adhesive 87 leads to variation in amount of the penetrating adhesive 87 among the gaps between the adsorbing foil strips 82. That is, it is difficult to apply the adhesive 87 uniformly to the plate absorber 84, which fails to ensure uniform penetration of the adhesive 87 into each gap. Consequently, some gaps have a large amount of the adhesive 87 penetrating thereinto to cause the curing strain, and others have an extremely small amount of the adhesive tape penetrating thereinto to cause reduction in mechanical strength of the absorber 84. In order to avoid insufficient mechanical strength of the absorber 84, a sufficient amount of the adhesive 87 eventually has to be applied to the absorber 84 so as to spread round every gap. As a result, the absorbing foil strips 82 have a penalty in arrangement regularity.

On the other hand, it is impossible to have a configuration in which no adhesive 87 penetrates the gap between the absorption foil strips 82. That is because the absorbing foil strips 82 may be deformed when the seat covers 85, 86 cover the absorber 84 and the absorbing foil strips 82 are cut at both ends thereof. A round-blade cutter moves in an arrangement direction of the absorbing foil strips for cutting the absorbing foil strips 82 at both ends thereof. In this case, the absorbing foil strips 82 yield to be deformed due to shearing stress therein from the round-blade cutter, since the absorbing foil strips 82 have no adhesive 87 penetrating the gap therebetween. That is even when an influence of the curing strain may be avoided, the absorbing foil strips 82 at the end of the absorber 84 will vary in arrangement due to another inconvenience where the absorbing foil strips 82 has insufficient mechanical strength as noted above. Moreover, the absorber 84 formed in such manner is mechanically brittle. Accordingly, the absorbing foil strips 82 may lose its adhesion at worst.

Such problems from the curing strain may be solved mostly with the absorbing foil strips 82 having an increased length. That is, the absorber 84 has the absorbing foil strips 82 with extreme strain at the end thereof. Consequently, this region is taken off from a field of view of the fluoroscopic image. In other words, a radiation air grid is prepared having a sufficient width than the field of view. On the other hand, such radiation air grid has an increased size, which leads to troubles in provision of the radiation air grid for the fluoroscopic images. Moreover, the longer absorbing foil strips 82 have difficulty in pulling thereof linearly for parallel arrangement. Furthermore, the absorbing foil strips 82 extend to an end without entering into the field of view, and thus more molybdenum material is needed for forming the radiation air grid, which leads to high costs. Furthermore, where the absorbing foil 82 is serpentine, nonlinearity of the absorbing foil 82 is given throughout the absorbing foil strip 82. Accordingly, the above design variation cannot solve the problem sufficiently on difficulty in making the absorbing foil strips 82 linear. That is, it is more desirable to suppress strain itself at the end of the absorbing foil strips 82.

This invention has been made regarding the state of the art noted above, and its object is to provide a radiation grid without obstructing travel of direct radiation by arranging regularly absorbing foil strips having a maintained linear shape.

Means for Solving the Problem

This invention is configured as stated below in order to achieve the above object. A radiation grid according to this invention includes an absorber having strip absorbing foil strips that extend in an extension direction for absorbing radiation arranged in an arrangement direction perpendicular to the extension direction, and having an incident plane where radiation enters and an emitting plane where radiation emits; a first covering member for covering one plane of the incident plane or the emitting plane of the absorber; a second covering member for covering the other plane other than the one plane of the absorber; a first joining member arranged at a contact portion of each absorbing foil strip constituting the absorber and the first covering member for providing integration of both thereof; and a second joining member arranged at a contact portion of each absorbing foil strip constituting the absorber and the second covering member for providing integration of both thereof. A gap is provided between the first joining member and the second joining member. The first joining member has a thickness larger at both ends thereof in the extension direction than a center portion between the both ends.

OPERATION AND EFFECT

The radiation grid of this invention has the absorber with the arranged strip absorbing foil strips. The absorber maintains its shape through integration with the first covering member via the first joining member and with the second covering member via the second joining member. Here, the first joining member and the second joining member are formed by hardening a gelatinous adhesive, which inherently leads to curing strain. According to the radiation grid of this invention, however, the gap is provided between the first and second joining members. Consequently, curing strain may be suppressed as much as possible that occurs upon curing of both joining members. Provision of the gap between the both joining members may result in a less amount of adhesive used for manufacture of the radiation grid by that in the gap. Accordingly, less curing strain may occur by reduced adhesive.

The absorbing foil strips of the radiation grid according to this invention may be securely supported at both ends thereof. That is because the first joining member has a thickness larger at both ends thereof in the extension direction than the center portion between the both ends. The both ends of the absorbing foil strips in the extension direction have to be supported securely for realizing linearity and regular arrangement of the absorbing foil strips. In addition, according to the configuration of this invention, a thick portion of the first joining member supports the both ends of the absorbing foil strips in the extension direction. Consequently, the radiation grid has enhanced strength.

Moreover, direct radiation may efficiently pass through the radiation grid of this invention. That is because the first joining member has a smaller thickness in the center portion thereof. When a shadow of the first joining member falls on a fluoroscopic image of a subject, visibility in the radiological image may be reduced, accordingly. On the other hand, according to the configuration of this invention, the first joining member has a thickness possibly suppressed in the center portion thereof. Consequently, the first joining member does not prevent direct radiation from traveling that falls on the fluoroscopic image of the subject.

Moreover, in the foregoing configuration, the second joining member has a thickness larger at both ends thereof in the extension direction than the center portion between the both ends.

The radiation grid of the foregoing configuration has enhanced strength. That is, the first and second joining members support the absorbing foil strips. Here, the second joining member has a thickness larger at both ends thereof in the extension direction than the second joining member in the center portion between the both ends. In other words, the second joining member of the foregoing configuration has the same effect as the first joining member.

Moreover, at both ends of the first joining member in the extension direction of the foregoing configuration, the first joining member extends in a gap between the absorbing foil strips adjacent to each other for connecting the adjacent absorbing foil strips. Such configuration is more desirable.

Moreover, at both ends of the second joining member in the extension direction of the foregoing configuration, the second joining member extends in a gap between the absorbing foil strips adjacent to each other for connecting the adjacent absorbing foil strips. Such configuration is more desirable.

According to the foregoing configuration, even when the absorbing foil strips in the radiation grid are cut to have an even length in the extension direction in manufacture of the radiation grid, the absorber never yields to be deformed due to shearing stress therein upon cut of both ends of the absorbing foil strips. That is, the first and second joining members extend in the gap between the absorbing foil strips adjacent to each other, thereby connecting the adjacent absorbing foil strips to each other in its arrangement direction. When the radiation grid is cut at the both ends thereof to have an even length in such state, no absorbing foil strip is deformed. That is because the absorbing foil strips adjacent to each other are secured with the first and second joining members in its arrangement direction.

Moreover, the radiation grid may be provided in the radiographic apparatus. That is, the radiographic apparatus of this invention having the radiation grid provided therein may include a radiation source for emitting radiation beams; a radiation detecting device for detecting radiation beams to form detection signals; a radiation grid arranged so as to cover a radiation detection surface where the radiation detecting device detects radiation; an image formation device for forming an original image based on the detection signals; and a trimming device for cutting off a given region in the original image to form a fluoroscopic image. The given region in the original image is a region where a shadow of both ends in the radiation grid falls. Such configuration is preferable.

According to the foregoing configuration, the image formation device forms the original image. The image, however, is not directly used for diagnosis. That is, the foregoing configuration includes the trimming device for cutting off both ends of the image to form the fluoroscopic image. Here, the shadow of both ends of the first joining member falls on the given region in the original image. The both ends are to absorb more radiation taking into consideration that they are thick. According to the foregoing configuration, however, the given region where both ends of the first joining member fall is cut off to form the fluoroscopic image. Consequently, the fluoroscopic image finally obtained has no shadow of both ends of the first joining member falling thereon.

EFFECT OF THE INVENTION

According to the radiation grid of this invention, the gap is provided between the first and second joining members, which results in possibly suppressed curing strain that occurs upon curing of both joining members. Provision of the gap between the both joining members may result in a less amount of adhesive used for manufacture of the radiation grid by that in the gap. Accordingly, less curing strain may occur by reduced adhesive.

Moreover, the radiation grid of this invention has sufficient strength. That is because the first and second joining members have a thickness at both ends thereof in the extension direction larger than the center portion thereof between the both ends, respectively. In addition, according to the configuration of this invention, thick portions of the first and second joining members support the both ends of the absorbing foil strips in the extension direction. Consequently, the radiation grid has enhanced strength. Moreover, direct radiation may efficiently pass through the radiation grid of this invention. That is because the first and second joining members have a smaller thickness in the center portion thereof, respectively. According to the configuration of this invention, the first and second joining members have a thickness possibly suppressed in the center portion thereof. Consequently, the first joining member does not prevent direct radiation from traveling that falls on the fluoroscopic image of the subject.

BRIEF DESCRIPTION OF THE DRAWINGS

FIG. 19 is a schematic view showing operations of the X-ray apparatus according to Embodiment 2.

DESCRIPTION OF REFERENCES

1 X-ray grid (radiation grid)
10 absorber
10a absorbing foil strip
11 first seat cover (first covering member)
12 second seat cover (second covering member)
15 first joining member
16 second joining member
52 FPD (radiation detecting device)
53 X-ray tube (radiation source)
54 X-ray grid (radiation grid)
60 image formation section (image formation device)
61 trimming section (trimming device)

BEST MODE FOR CARRYING OUT THE INVENTION

Embodiments suitable for implementation of this invention will be described hereinafter with reference to the drawings.

Embodiment 1

Figure 1:
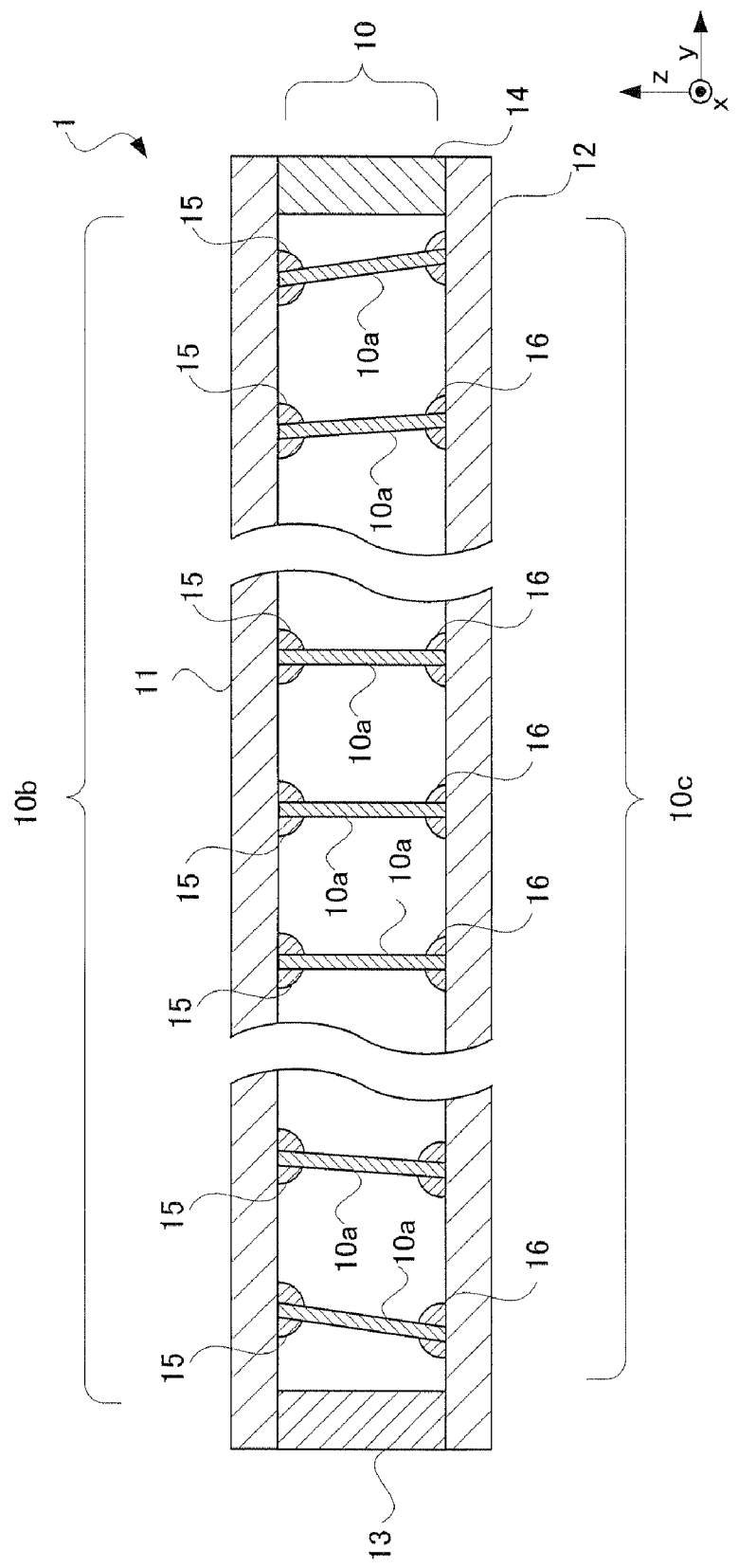
FIG. 1 is a sectional view showing a configuration of an X-ray grid according to Embodiment 1.

FIG. 1 is a sectional view showing a configuration of an X-ray grid according to Embodiment 1. As shown in FIG. 1, an X-ray grid 1 according to Embodiment 1 includes an absorber 10 having absorbing foil strips 10a arranged in a y-direction, a first seat cover 11 for covering an upper surface of the absorber 10, a second seat cover 12 for covering an undersurface of the absorber 10, a first side post 13 and a second side post 14 extending in an x-direction. Moreover, the absorber 10 includes an incident plane 10b where X-rays enter and an emitting plane 10c where X-rays emit.

The absorber 10 has absorbing foil strips 10a extending in the x-direction. The absorbing foil strips 10a are arranged in the y-direction perpendicular to the x-direction and, when seen as the entire X-ray grid are arranged as in a window blind. The arrangement pitch thereof is 500 μm, for example. The absorbing foil strips 10a are formed of a molybdenum alloy that absorbs X-rays. The y-direction here corresponds to the arrangement direction in this invention. Directing attention to any one of the absorbing foil strips 10a, the x-direction corresponds to the extension direction for an absorbing foil strip 10a, the v-direction to the thickness direction for the absorbing foil strip 10a, and the z-direction to the width direction for the absorbing foil strip 10a. Here, the x-direction, the y-direction, and the z-direction are perpendicular to one another.

Next, inclination of the absorbing foil strips 10a will be described. As shown in FIG. 1, the absorbing foil strips 10a in the absorber 10 have gradual inclination toward the end of the absorber in the y-direction. As noted above, the absorbing foil strips 10a provided in the X-ray grid 1 of Embodiment 1 vary in inclination such that X-rays spreading radially pass through them upon incidence of X-rays in a cone shape.

The X-ray grid 1 has the plate first seat cover 11 that covers the incident plane 10b of the absorber 10. Moreover, the second seat cover 12 is provided so as to cover the emitting plane 10c of the absorber 10 in the z-direction. Both seat covers 11, 12 are composed of glass fiber easy to transmit X-rays. Here, the first seat cover and the second seat cover correspond to the first covering member and the second covering member, respectively, of this invention.

The first seat cover 11 is adhered to each of the absorbing foil strips 10a constituting the absorber 10. That is, a contact portion where the first seat cover 11 contacts the absorbing foil strip 10a has a first joining member 15 fixedly attached thereto that is composed of a cured adhesive. In other words, the first joining member 15 is provided on the contact portion of the first seat cover 11 and the incident plane 10b of the absorber 10. The first joining member 15 is fixedly attached to one side of the absorbing foil strip 10a along the extension direction. Accordingly, the first joining member 15 has a shape where bars extending in the x-direction are arranged in the v-direction. The first joining member 15 is also fixedly attached to the first seat cover 11. That is, the first seat cover 11 is integrated with the absorbing foil strips 10a via the first joining member 15.

Likewise, the second seat cover 12 is adhered to each of the absorbing foil strips 10a constituting the absorber 10. In other words, a second joining member 16 is provided on the contact portion of the second seat cover 12 and the emitting plane 10c of the absorber 10. That is, a contact portion where the second seat cover 12 contacts the absorbing foil strip 10a has the second joining member 16 fixedly attached thereto that is composed of a cured adhesive. The second joining member 16 is fixedly attached to the other side of the absorbing foil strip 10a, different from the one side thereof, along the extension direction. Accordingly, the second joining member 16 has a shape where bars extending in the x-direction are arranged in the y-direction. The second joining member 16 is also fixedly attached to the second seat cover 12. That is, the second seat cover 12 is integrated with the absorbing foil strips 10a via the second joining member 16.

The first side post 13 and the second side post 14 are prism members extending in the x-direction. The first side post 13 is provided at one end of the absorber 10 in the x-direction. The second side post 14 is provided at the other end of the absorber 10 opposite to the one end in the x-direction. The first side post 13 and the second side post 14 are provided between both seat covers 11, 12. The first and second side posts 13, 14 form both ends of the X-ray grid 1 in the x-direction, and fix both seat covers 11, 12 for playing a role for provision of the rugged X-ray grid 1.

Figure 2:
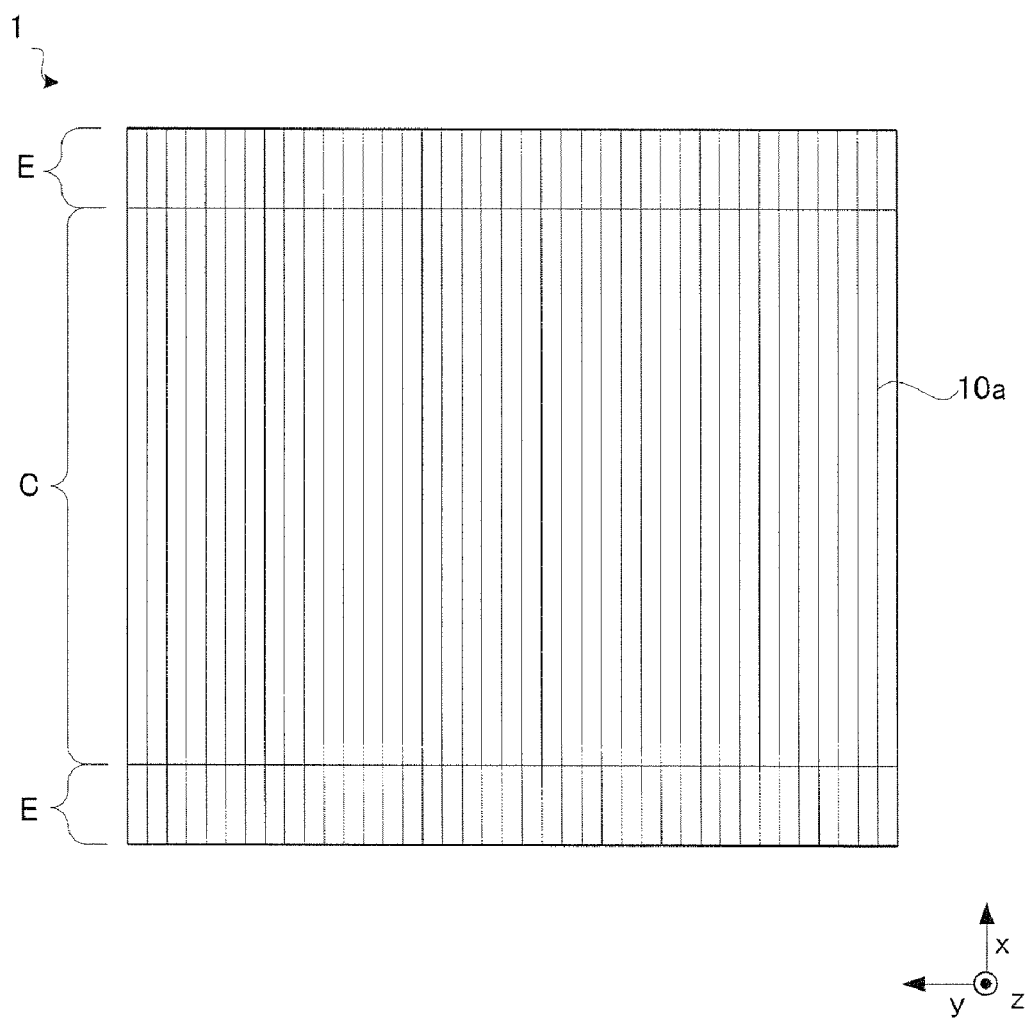
FIG. 2 is a plan view showing a configuration of the X-ray grid according to Embodiment 1.

FIG. 2 is a plan view showing a configuration of the X-ray grid according to Embodiment 1. When seen in the z-direction, the X-ray grid 1 has ends in the x-direction where ends E of the first joining member 15 extend, as shown in FIG. 2. Likewise, the X-ray grid 1 has a center portion in the x-direction where a center portion C of the first joining member 15 extends.

Figure 3:
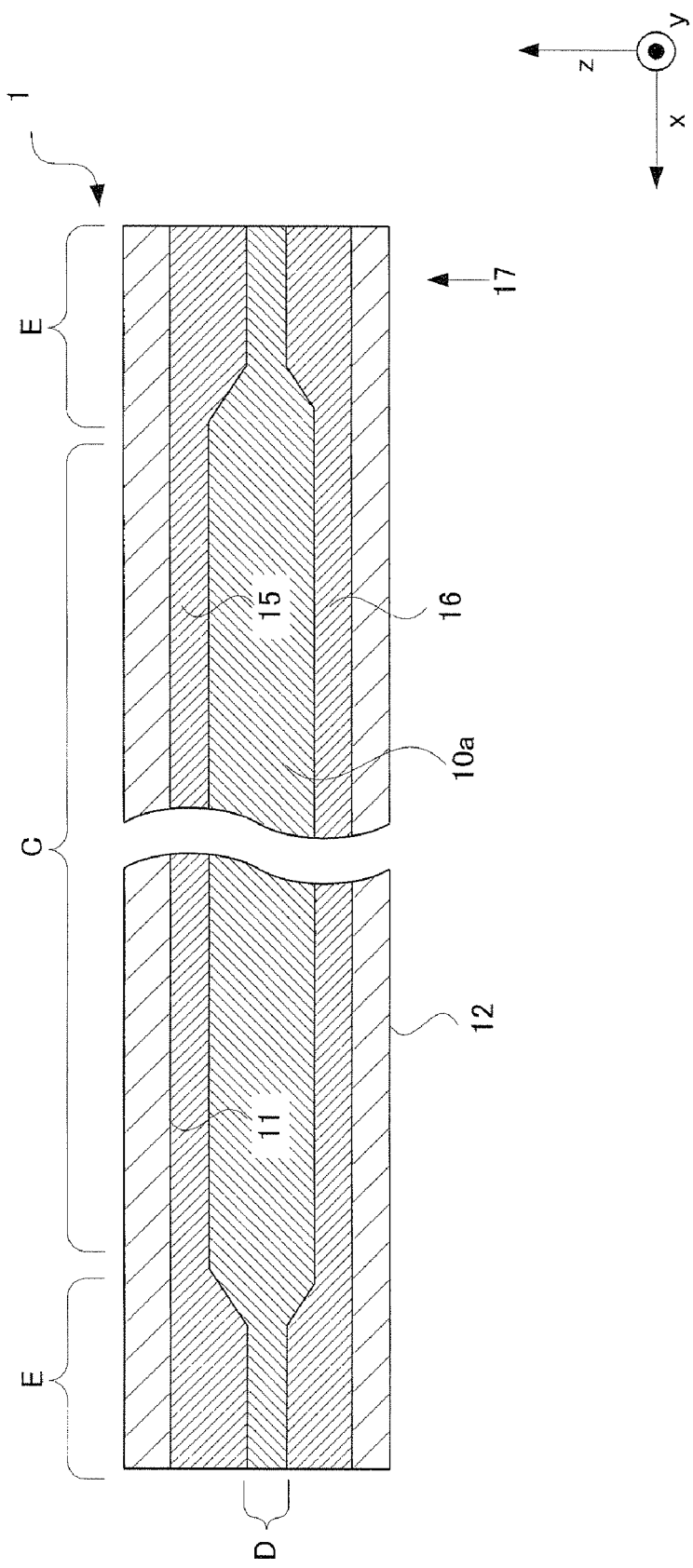
FIGS. 3 and 4 are sectional views each showing a shape of a joining member according to Embodiment 1.

Description will be given of a shape of the first joining member 15 as the most characteristic part in this invention. FIG. 3 is a sectional view showing a shape of the joining member according to Embodiment 1. As shown in FIG. 3, the first joining member has a thickness larger at the ends E thereof in the z-direction than the center portion C in the z-direction. Accordingly, the adhesive strength of the first seat cover 11 and the absorbing foil strip 10a is larger at the ends E of the first joining member 15 than that in the central portion C of the first joining member 15. The center portion C of the first joining member 15 has a thickness in the z-direction of 0.1 mm-0.15 mm, for example. The both ends E of the first joining member 15 have a thickness in the z-direction of 1 mm-2 mm, for example. In addition, the absorbing foil strip 10a has a width in the z-direction of 5.7 mm, for example.

Moreover, a gap D is provided between the first joining member 15 and the second joining member 16. Accordingly, the first joining member 15 and the second joining member 16 are not directly connected.

Figure 4:
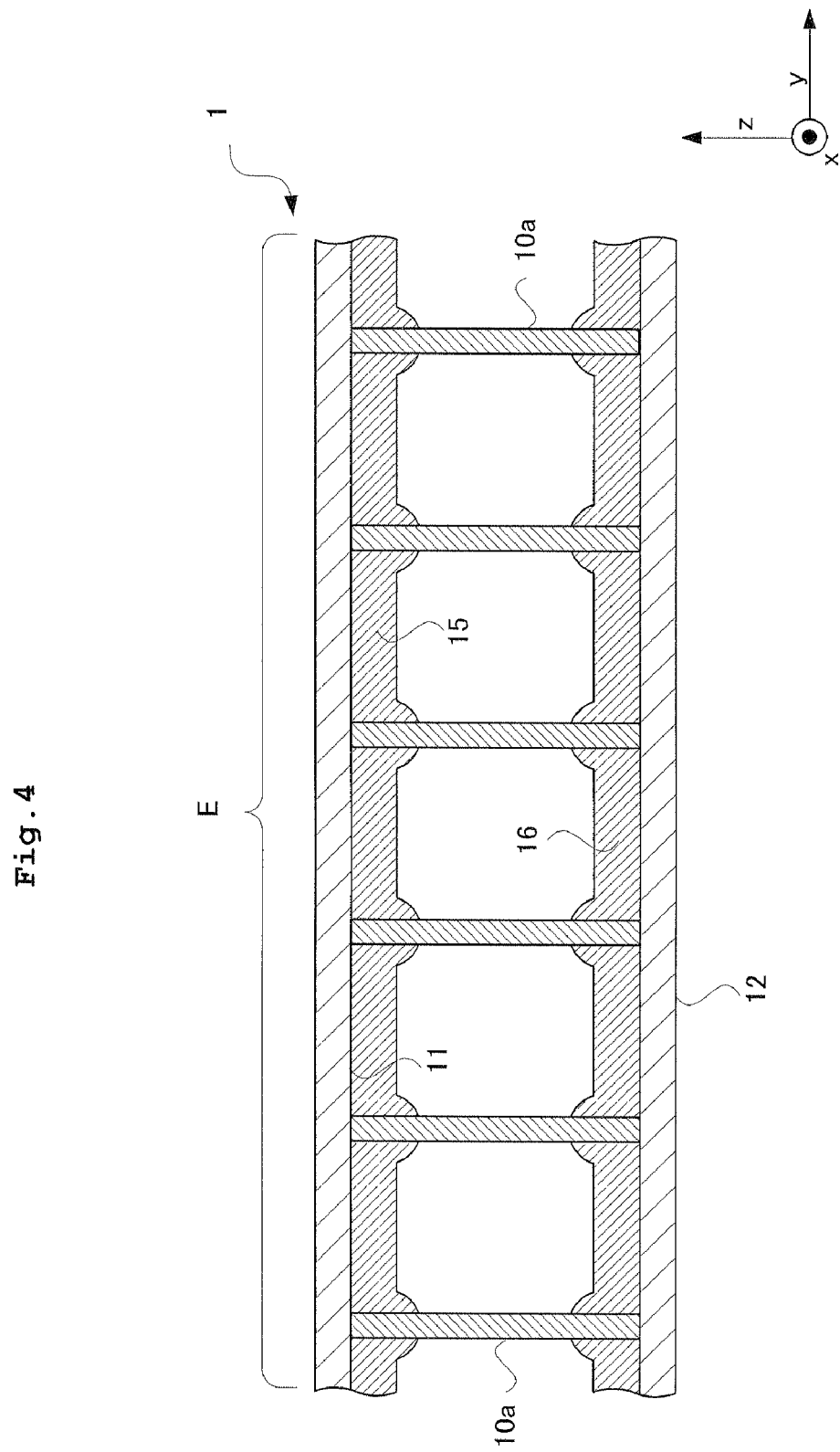

Further description will be given of the configuration of the first joining member 15. FIG. 4 is a sectional view showing a shape of the joining member according to Embodiment 1. FIG. 4 shows a configuration here the X-ray grid is cut at a position illustrated by an arrow 17 in FIG. 3. Specifically, FIG. 4 shows a configuration of the end E in the first joining member 15 in the x-direction. As shown in FIG. 4, the first joining member 15 extends at the end B thereof so as to penetrate the gap between the absorbing foil strips adjacent to each other. The first joining member 15 is fixedly attached to one side of the absorbing foil strip 10a along the extension direction. Accordingly, the absorbing foil strips 10a adjacent to each other are connected via the first joining member 15. When seen this state as a whole of the X-grid, all absorbing foil strips 10a are integrated together via the first joining member 15.

The second joining member 16 has the same configuration as the foregoing first joining member 15. That is, as shown in FIG. 3, the second joining member 16 has a thickness larger at the ends E thereof in the z-direction than the center portion C in the z-direction. Accordingly, the adhesive strength of the second seat cover 12 and the absorbing foil strip 10a is larger at the ends E of the second joining member 16 than that in the center portion C of the second joining member 16. Moreover, as shown in FIG. 4, the second joining member extends at the end E thereof so as to penetrate the gap between the absorbing foil strips adjacent to each other. The second joining member 16 is fixedly attached to the other side of the absorbing foil strip 10a along the extension direction. Accordingly, the absorbing foil strips 10a adjacent to each other are connected via the second joining member 16. When seen this state as a whole of the X-grid, all absorbing foil strip 10a are integrated together via the second joining member 16.

Figure 5:
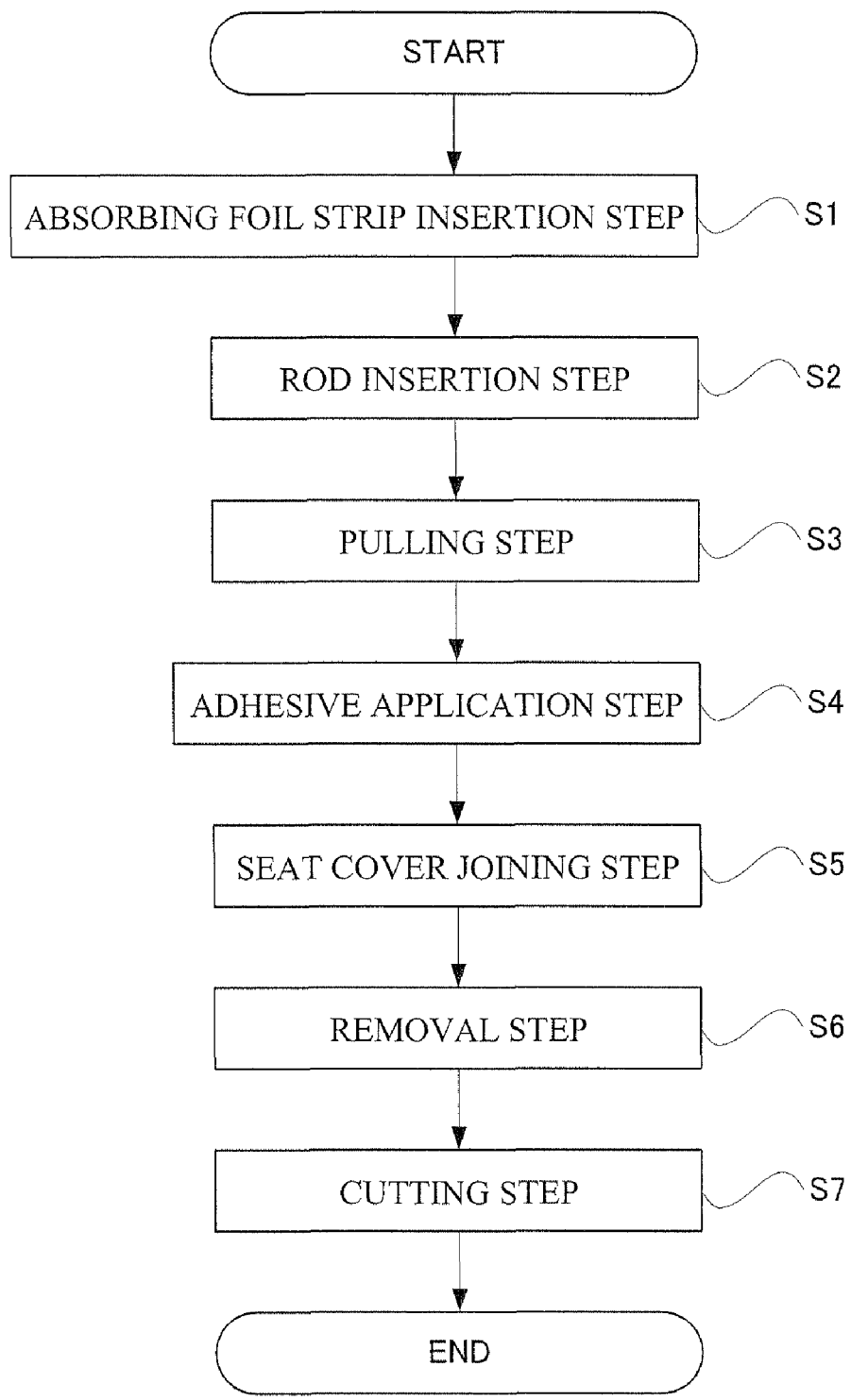
FIG. 5 is a flow chart showing a method of manufacturing the X-ray grid according to Embodiment 1.

Next, description will be given of a manufacturing method of the X-ray grid according to Embodiment 1. FIG. 5 is a flow chart showing a method of manufacturing the X-ray grid according to Embodiment 1. The method of manufacturing the X-ray grid 1 includes an absorbing foil strip insertion step S1 for inserting absorbing foil strips 10a into comb plates 23 and 24 provided on an arrangement table 21 for absorbing foil strips; a rod insertion step S2 for inserting a first rod 27 and a second rod 28 into through holes 10d and 10e, respectively, provided at both ends of the absorbing foil strips 10a; a pulling step S3 for pulling the absorbing foil strips 10a collectively through giving tension to the first rod 27; an adhesive application step S4 for applying an adhesive 39, prior to curing, to both plate seat covers 11, 12; a seat cover joining step S5 for joining the both seat covers 11, 12 to an absorber 10; a removal step S6 for removing the X-ray grid 1 from the arrangement table 21 for absorbing foil strips; and a cutting step S7 for cutting the both ends of the X-ray grid to an even length. Each of these steps will be described in order.

<Absorbing Foil Strip Insertion Step S1>

Figure 6:
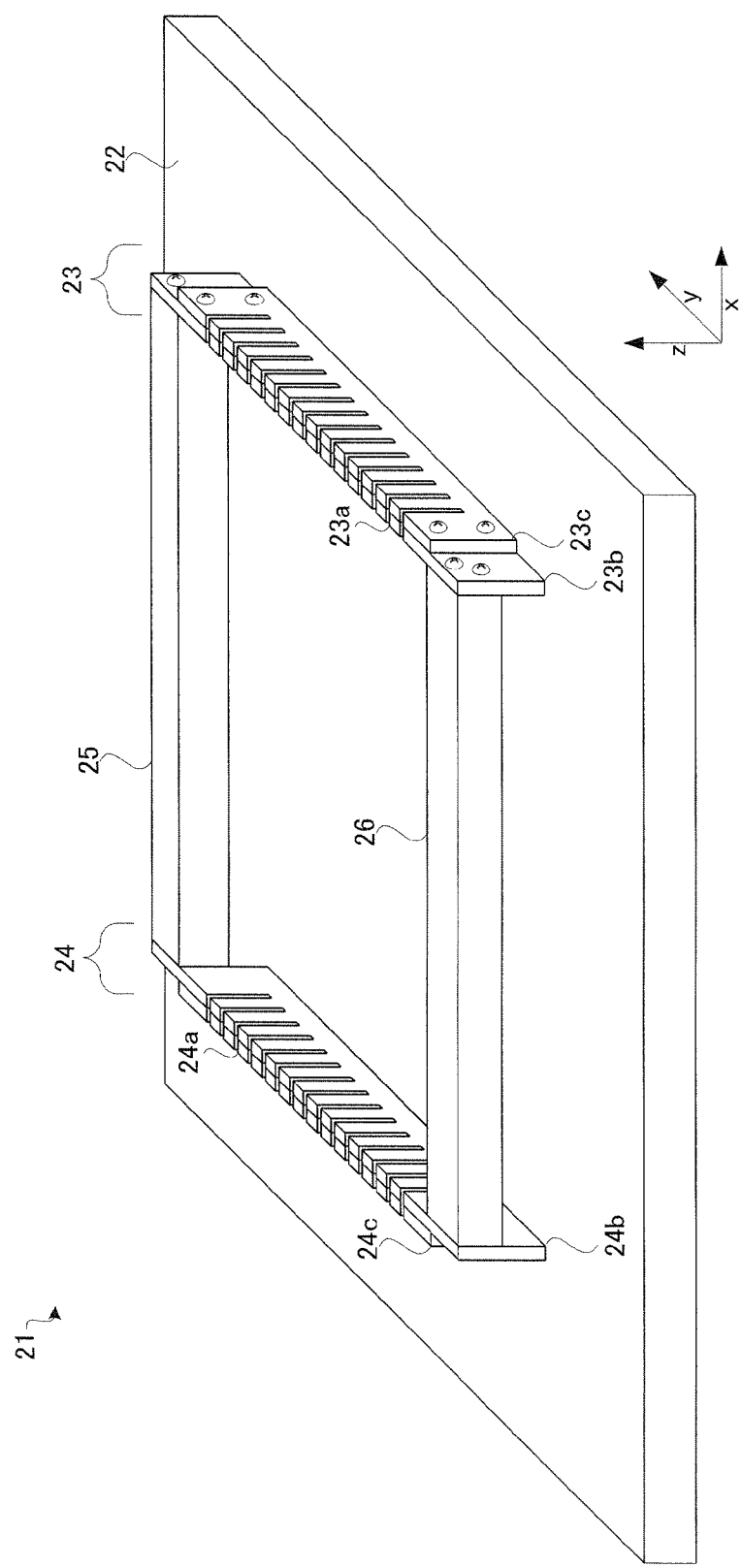
FIG. 6 is a perspective view showing an arrangement table for absorbing foil strips according to Embodiment 1.

Firstly, description will be given of the arrangement table 21 for absorbing foil strips according to Embodiment 1 prior to explanation on the absorbing foil strip insertion step. FIG. 6 is a perspective view showing an arrangement table for absorbing foil strips according to Embodiment 1. As shown in FIG. 6, the arrangement table 21 for absorbing foil strips has a pair of comb plates 23, 24 that is fixed to a base 22. The comb plates 23, 24 are elongate members extending in the y-direction, and have grooves 23a, 24a extending approximately in the z-direction. The grooves 23a, 24a are provided so as to pass through the comb plates 23, 24, respectively, in the x-direction and to have an equal arrangement pitch in the y-direction. Each of the comb plates 23, 24 is provided in the arrangement table 21 for absorbing foil strips so as to be directed to each other. The grooves 23a, 24a have absorbing foil strips 10a having a thickness of 30 μm inserted thereinto, which is to be mentioned later. Here, the comb plates 23, 24 are removablly fixed to the base 22.

Each of the comb plates 23, 24 are screwed for fixation to struts 25, 26 extending in the x-direction. That is, each of the comb plates 23 and 24 is connected via the struts 25 and 26. The struts 25, 26 are provided at the ends of the comb plates 23, 24 in the y-direction. The four members, i.e., the comb plates 23, 24 and the struts 25, 26, are arranged rectanglarly to form a frame having a rectangular space at a center portion thereof. Here, the strut 25 does not contact the base 22. Accordingly, a gap is provided between the strut 25 and the base 22. Moreover, the arrangement table 21 for absorbing foil strip has various members outside the frame, which is to be mentioned later.

Figure 7:
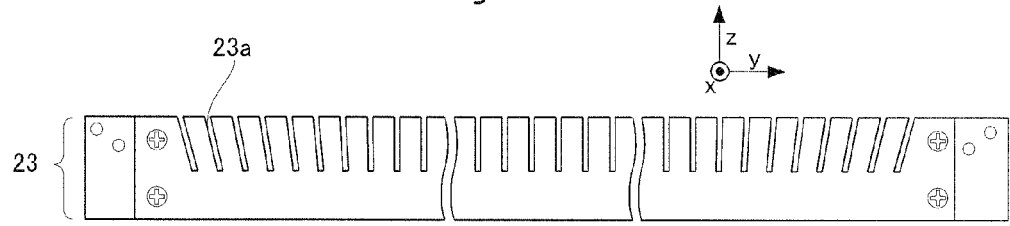
FIG. 7 is a plan view showing a configuration of a comb plate according to Embodiment 1.

Further description will be given of the comb plates 23, 24. FIG. 7 is a plan view showing a configuration of the comb plate according to Embodiment 1. As shown in FIG. 7, the comb plate 23 has two or more grooves 23a extending approximately in the z-direction. The grooves 23a have gradual inclination from the center toward the ends of the comb plate 23. Specifically, each of the grooves 23a at the ends of the comb plate 23 is inclined such that the opening thereof is away from the center portion of the comb plate 23. If the grooves 23a extend, they all concentrate on one point. This will be called a concentrating point, which meaning is to be mentioned later.

Figure 8:
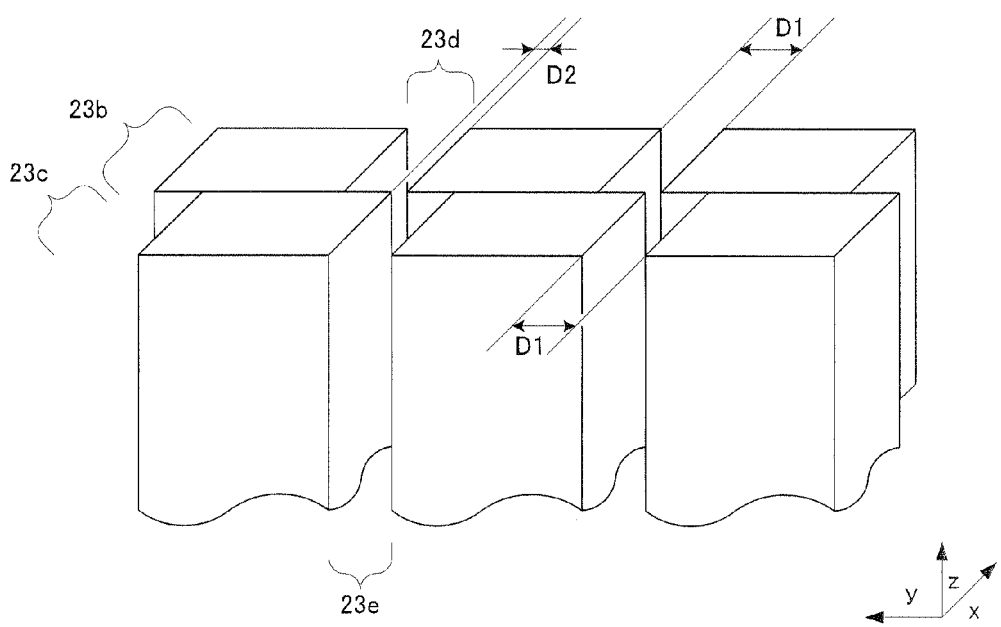
FIG. 8 is a perspective view showing a configuration of the comb plate according to Embodiment 1.

The comb plate 23 has two members integrated with each other. That is, as shown in FIG. 6, the comb plate 23 has a configuration in which a main plate 23b extending in the y-direction and a sub plate 23c similarly extending in the y-direction with a smaller length than the main plate 23a are screwed for integration. Specifically, both ends of the sub plate 23c in the y-direction are screwed on the main plate 23b. The main plate 23b and the shorter sub plate 23c have grooves provided therein in approximately the z-direction. They are connected to form the grooves 23a of the comb plate 23. FIG. 8 is a perspective view showing a configuration of the comb plate according to Embodiment 1. As shown in FIG. 8, the grooves 23d of the main plate 23b deviate from the grooves 23e of the sub plate 23c in position in the y-direction. Here, the grooves 23d, 23e have a width D1 in the y-direction of 100 μm. The width D1 is approximately three times of the thickness of the absorbing foil strip 10a. Accordingly, insertion of the absorbing foil strips 10a into the grooves 23d causes loose fitting of the absorbing foil strips 10a in the y-direction. However, the grooves 23d deviate from the grooves 23e in Embodiment 1 by 70 μm in the y-direction. Consequently, a distance between a side surface of the groove 23e forwardly in the y-direction and that of the groove 23d backward in the y-direction is 30 μm, which is equal to the thickness of the absorbing foil strips. Accordingly, insertion of the absorbing foil snips 10a into the comb plate 23 may cause no loose fitting in the y-direction. Here, the comb plate 24 has the same configuration as the comb plate 23. That is, the comb plate 24 has grooves 24 inclined as noted above. Moreover, the comb plate 24 has a main plate 24b and a sub plate 24c.

Figure 9:
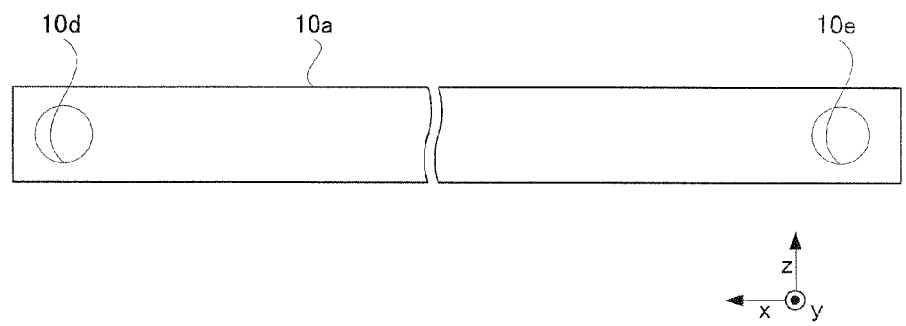
FIG. 9 is a perspective view showing a configuration of an absorbing foil strip according to Embodiment 1.

FIG. 9 is a perspective view showing a configuration of the absorbing foil strip according to Embodiment 1. As shown in FIG. 9, the absorbing foil strips 10a are in a strip shape extending in the x-direction, and has through holes 10d, 10e provided at both ends thereof in the x-direction for insertion of rods 27, 28, mentioned later.

Figure 10:
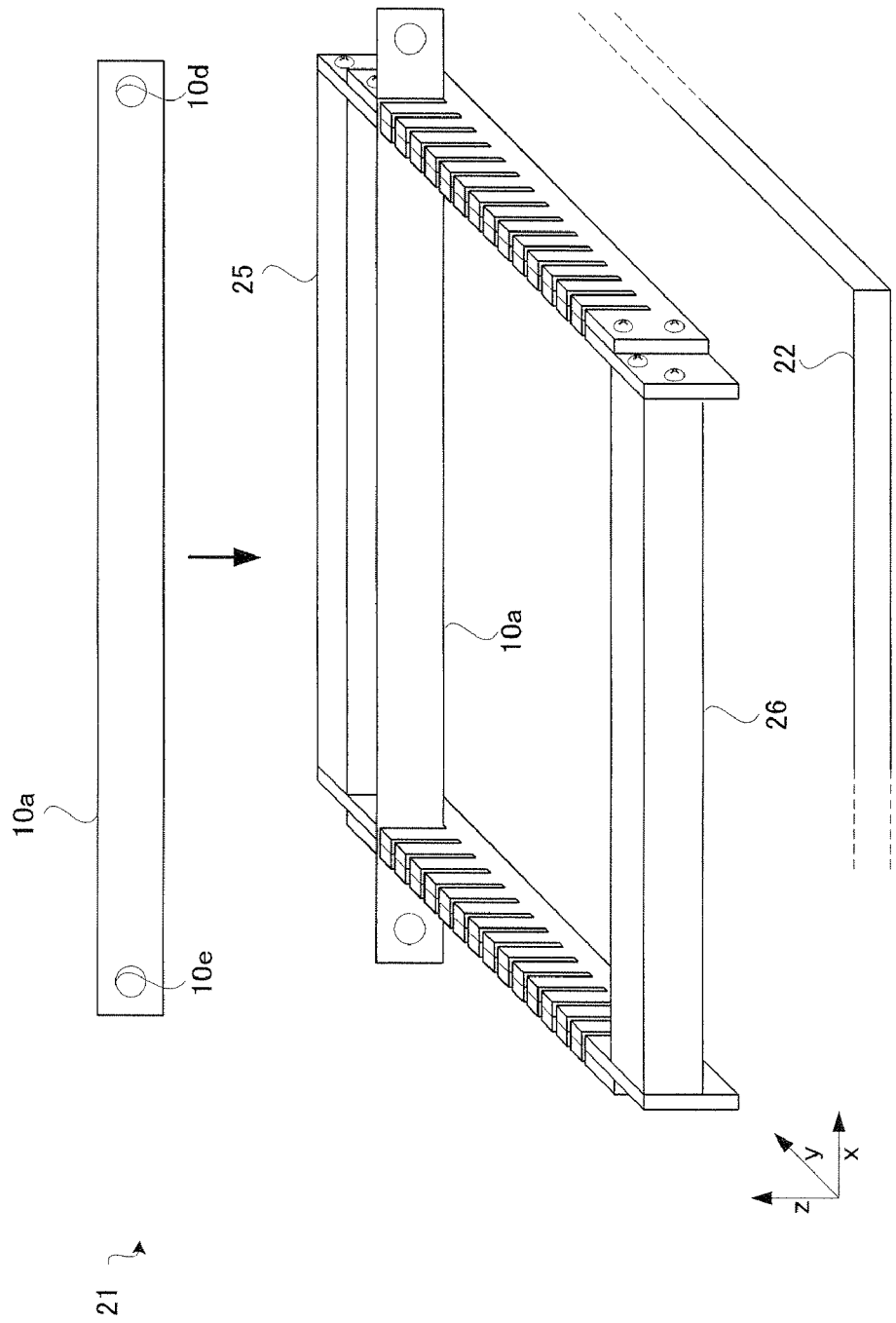
FIG. 10 is a perspective view showing a step of inserting the absorbing foil strips according to Embodiment 1.

FIG. 10 is a perspective view showing a step of inserting the absorbing foil strips according to Embodiment 1. As shown in FIG. 10, in the absorbing foil insertion step S1, the absorbing foil strips 10a are actually inserted into the grooves 23a of the comb plate 23 and the grooves 24a of the comb plate 24 in the z-direction. Accordingly, the absorbing foil strips 10a are supported at both ends thereof. The absorbing foil strips 10a are not housed into the foregoing frame. The both ends of the absorbing foil strips 10a project outwardly from the frame. Consequently, the through holes 10d, 10e are located outside of the frame. The absorbing foil strip insertion step S1 is completed when the absorbing foil strips 10a are inserted into every groove 23a, 24a. At this time, approximately four hundred absorbing foil strips 10a are to be arranged in the y-direction.

<Rod Insertion Step S2>

Figure 11:
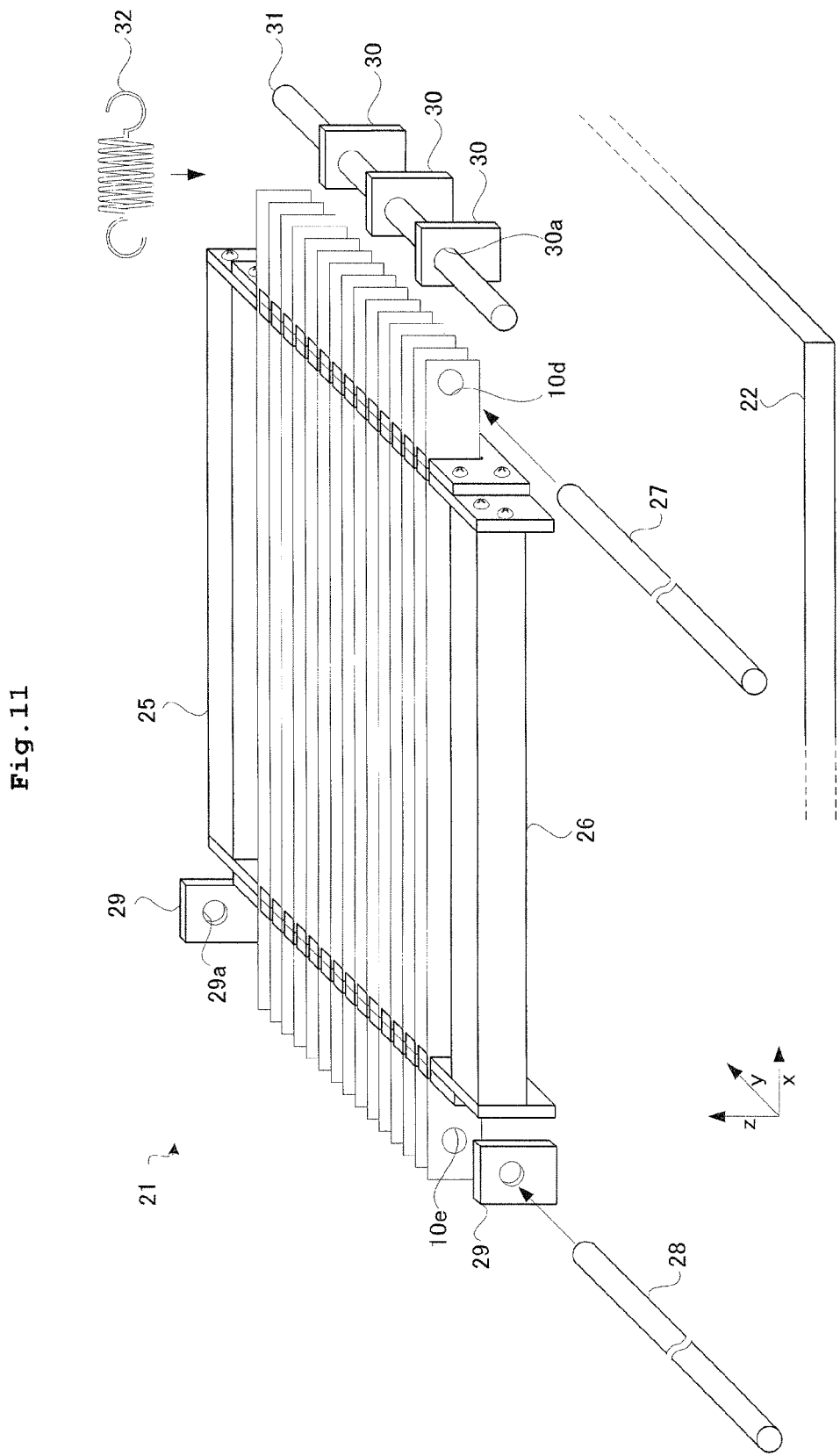
FIG. 11 is a perspective view showing a step of inserting a rod according to Embodiment 1.

Subsequently, the first rod 27 and the second rod 28 are inserted into the through holes 10d and 10e, respectively, of the absorbing foil strips 10a. FIG. 11 is a perspective view showing a step of inserting the rod according to Embodiment 1. Approximately four hundred absorbing foil strips 10a each have one through hole 10d having an almost equal position in the x-direction. Accordingly, as shown in FIG. 11, as the first rod 27 is inserted into the through hole 10d of the absorbing foil strip 10a located at the end thereof in the y-direction, the first rod 27 is similarly inserted into the through holes 10d of the other absorbing foil strips 10a. As noted above, insertion of the first rod 27 is performed collectively with respect to every absorbing foil strip 10a.

Moreover, the second rod 28 is inserted into the through holes 10e of the absorbing foil strips 10a. Insertion of the second rod 28 is performed collectively with respect to every absorbing foil strip 10a, which is similar to the first rod 27. Here, the second rod 28 is inserted not only into the absorbing foil strips 10a but also into two or more first fixtures 29 provided fixedly on the arrangement table 21 for absorbing foil strips. The first fixtures 29 are provided outside from the frame formed with the comb plates 23, 24 and the struts 25, 26, and provided adjacent to the comb plate 24. The first fixtures 29 are arranged in the y-direction. Moreover, the first fixtures 29 have through holes 29a extending in the v-direction and passing through the first fixtures 29. The second rod 28 is inserted into the through hole 29a, thereby being prevented from moving accordingly upon pulling of the absorbing foil strips 10a in the x-direction.

In addition, as shown in FIG. 11, the arrangement table 21 for absorbing foil strips has two or more second fixtures 30 fixedly provided thereon. Specifically, the second fixtures 30 are provided outside from the frame formed with the comb plates 23, 24 and the struts 25, 26, and provided adjacent to the comb plate 24. Since these members are important in the subsequent steps, description will be given of them. The second fixtures 30 are arranged in the y-direction. Moreover, the second fixtures 30 have through holes 30a extending in the y-direction and passing through the second fixtures 30. A third rod 31 is inserted into the through holes 30a in advance that extends in the y-direction.

<Pulling Step S3>

As is seen from FIG. 11, the first rod 27 and the third rod 31 are adjacent to each other. Accordingly, springs 32 may be provided between the first rod 27 and the third rod 31. In the pulling step S3, the absorbing foil strips 10a are pulled in the x-direction by use of the springs 32 as a tension device. The springs 32 are prepared having both ends in a J-shape hook for applying a tension. The spring 32 is hooked at one end thereof to the first rod 27, and at the other end to the third rod 31 so as to bridge the first rod 27 and the third rod 31. The springs 32 are provided to have an arrangement at equal intervals in the y-direction for application of a uniform tension to every absorbing foil strip 10a.

Figure 12:
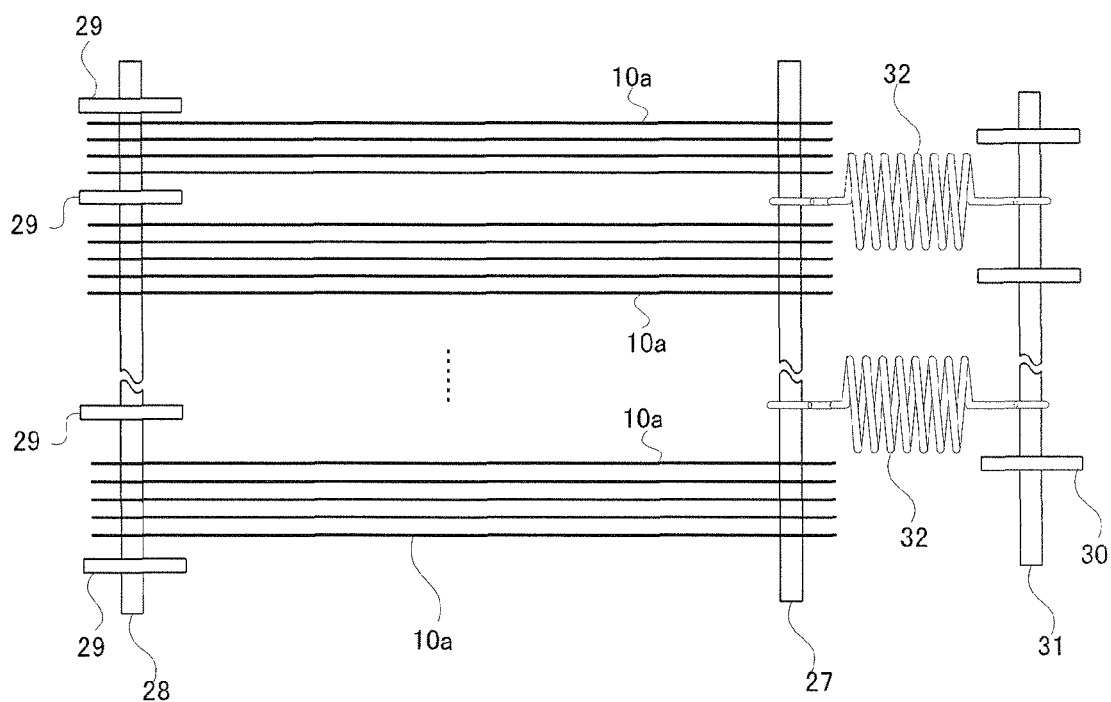
FIG. 12 is a plan view showing a pulling step according to Embodiment 1.

As noted above, every absorbing foil strip 10a is collectively pulled with both rods 27, 28, as shown in FIG. 12. In Embodiment 1, a tension is applied to the absorbing foil strips 10a, which results in linearity and more regular arrangement of the absorbing foil strips 10a. Accordingly, each absorbing foil strip 10a is arranged in the v-direction to form the absorber 10.

<Adhesive Application Step S4>

Figure 13:
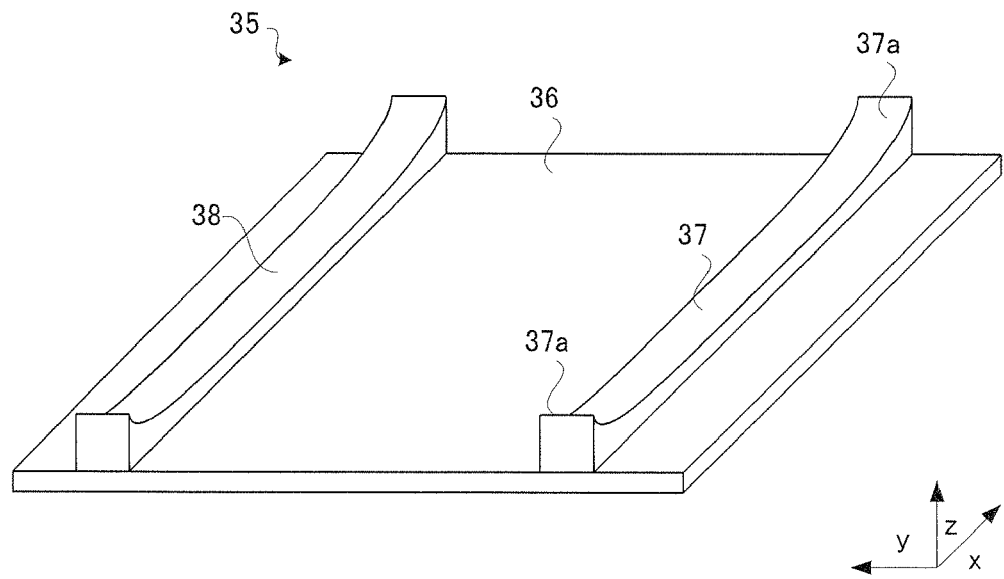
FIG. 13 is a perspective view showing a configuration of an adhesive shaping table according to Embodiment 1.

Subsequent to the pulling step S3, an adhesive is applied to the first seat cover 11. The adhesive shaping table 35 is used in the adhesive application step S4. FIG. 13 is a perspective view showing a configuration of the adhesive shaping table according to Embodiment 1. As shown in FIG. 13, the adhesive shaping table 35 according to Embodiment 1 has a bottom plate 36 having a pair of guide rails 37, 38 provided thereon that extends in the x-direction. A pair of guide rails 37, 38 has a sufficient distance therebetween in the y-direction. Accordingly, the first seat cover 11 may be placed in the gap between a pair of guide rails 37, 38.

The guide rail 37 has a characteristic shape. Specifically, the upper surface of the guide rail 37 in the z-direction is a curved smooth surface. That is the guide rail 37 has ends in the x-direction with a thick portion 37a larger in thickness in the z-direction than a center portion thereof. Moreover, the thick portion 37a has a thickness in the z-direction increasing from the center portion toward the side ends in the x-direction of the guide rail 37. Here, the guide rail 38 has the same configuration as above.

Figure 14:
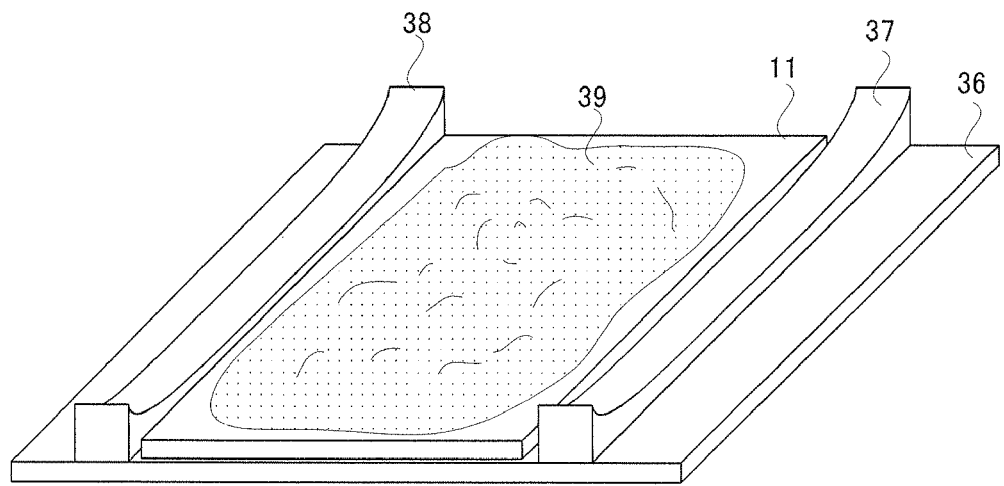
FIGS. 14 and 15 are perspective views each showing a step of applying an adhesive according to Embodiment 1.

FIG. 14 is a perspective view showing the step of applying the adhesive according to Embodiment 1. As shown in FIG. 14, the first seat cover 11 is placed on the bottom plate 36 of the adhesive shaping table 35. A gelatinous adhesive 39 prior to curing is applied to the upper surface of the first seat cover 11. Here, the adhesive 39 is desirable having physical properties of dispersal system with lost mobility.

Figure 15:
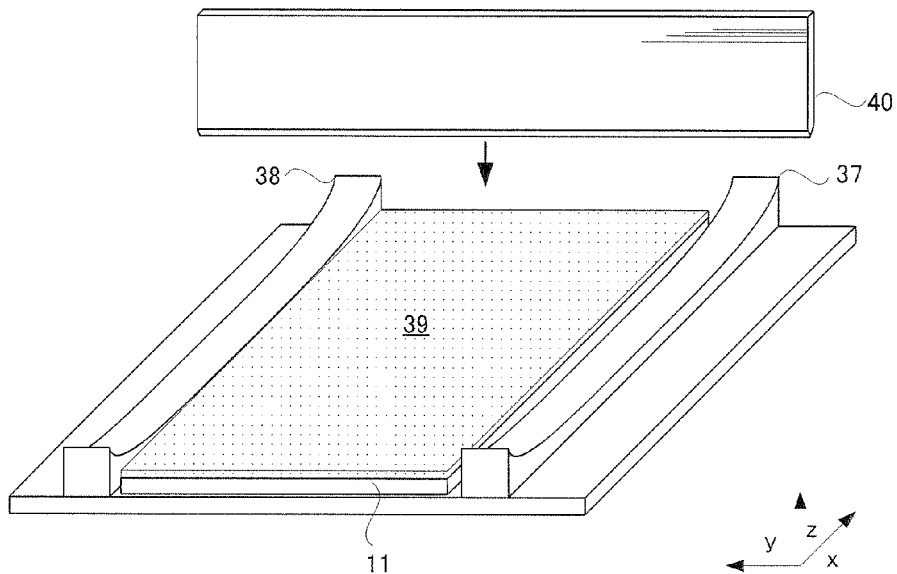
Figure 16:
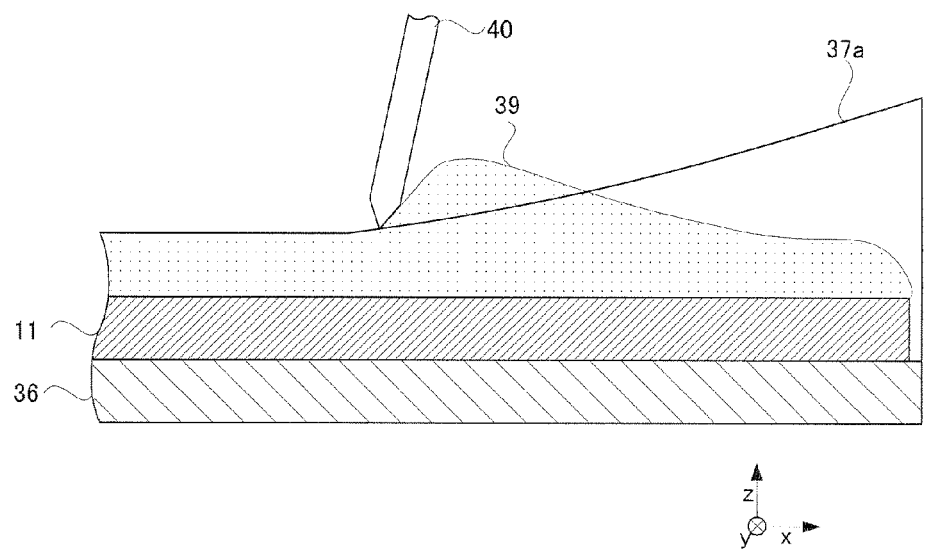
FIG. 16 is a sectional view showing the step of applying the adhesive according to Embodiment 1.

FIG. 15 is a perspective view showing the step of applying the adhesive according to Embodiment 1. As shown in FIG. 15, the adhesive 39 on the first seat cover 11 is shaped by use of a spatula 40 extending in the y-direction. Specifically, the spatula 40 slides in the x-direction while contacting both guide rails 37, 38. Here, the spatula 40 slides from the center portions of the guide rails 37, 38 toward the ends thereof in the x-direction while collecting the adhesive 39. Consequently, the adhesive 39 collected with the spatula 40 is moved in the x-direction, as shown in FIG. 16. The thick portions 37a are provided at both ends of the guide rails 37, 38. Accordingly, collecting ability of the adhesive 39 of the spatula 40 has decreased gradually when reaching the thick portion 37a. As a result, the collected adhesive 39 remains at the side portions of the first seat cover 11 in the x-direction, thereby being thick in the z-direction. This portion is to be the ends E in the first joining member 15 mentioned above. This tapered shape of both guide rails 37, 38 is transferred in this way to the adhesive 39 on the first seat cover 11. In addition, the adhesive 39 on the second seat cover 12 is shaped similarly to that on the first seat cover 11.

<Seat Cover Joining Step S5>

Subsequently, the first seat cover 11 and the second seat cover 12 are joined to the upper and under surfaces of the absorber 10, respectively. Here, both seat covers 11, 12 are attached to the absorber 10 such that the surfaces of both seat covers 11, 12 having the adhesive 39 applied thereto contact the absorber 10. Thereafter, the adhesive 39 is cured. Accordingly, the adhesive 39 applied on the first seat cover 11 is to be the first joining member 15, and the adhesive 39 applied on the second seat cover 12 is to be the second joining member 16. As noted above, both joining members 15, 16 integrate each absorbing foil strip 10a. Accordingly, the first joining member 15 has a thickness larger at both ends E thereof in the x-direction of the absorbing foil strips 10a than the center portion C in the x-direction of the absorbing foil strips 10a. Here, the second seat cover 12 has the same configuration as above.

<Removal Step S6>

Subsequently, the springs 32 are removed from the arrangement table 21 for absorbing foil strips. Then, the first rod 27 and the second rod 28 are pulled out from the absorber 10. Thereafter, screw of the struts 25, 26 and the comb plates 23, 24 is released. Moreover, fixation of the base 22 and the comb plates 23, 24 is released. At this time, upon pulling of the comb plates 23, 24 in a direction away from the absorber 10 along an x-axis, both seat covers 11, 12 and the absorbing foil strips 10a are removed integrally from the arrangement table 21 for absorbing foil strips.

<Cutting Step S7>

Figure 17:
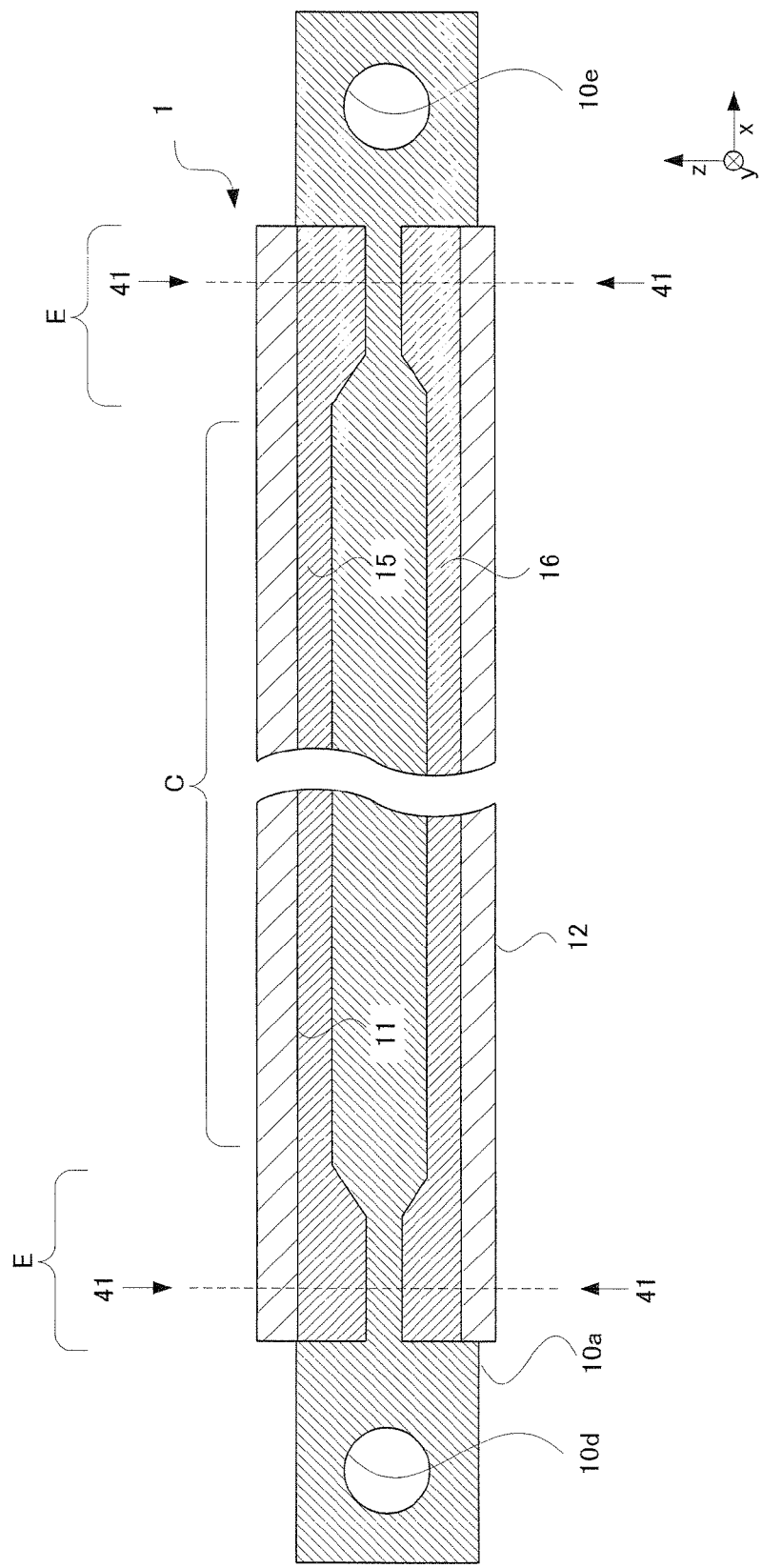
FIG. 17 is a sectional view showing a cutting step according to Embodiment 1.

Subsequently, the absorber 10 is cut at both ends thereof in the x-direction to have an even length. FIG. 17 is a sectional view showing the cutting step according to Embodiment 1. As shown in FIG. 17, the first joining member 15 and the second joining member 16 are cut at a position E shown by an arrow 41 on the ends E thereof. Here, a round-blade cutter moves in the y-direction for cutting the absorbing foil strips 10a at both ends thereof to be an equal length. Both ends of the absorbing foil strips 10a having the through holes 10d, 10e are cut out from the absorber 10. Finally, the first side post 13 and the second side post 14 extending in the x-direction are attached on both ends of the absorber 10 in the y-direction, whereby the X-ray grid 1 according to Embodiment 1 is completed.

As above, the X-ray grid 1 of Embodiment 1 has the absorber 10 with the arranged absorbing foil strips 10a. The absorbing foil strip 10a maintains its shape through integration of the absorber 10 with the first seat cover 11 via the first joining member 15 and with the second seat cover 12 via the second joining member 16. Here, the first joining member 15 and the second joining member 16 are formed through curing of the gelatinous adhesive 39, which inherently leads to curing strain. According, to the X-ray grid 1 of Embodiment 1, however, the gap is provided between the first joining member 15 and the second joining member 16. Consequently, curing strain may be possibly suppressed that occurs upon curing of both joining members 15, 16. Provision of the gap between the both joining members 15, 16 may result in a less amount of the adhesive 39 used for manufacture of the X-ray grid 1 by that in the gap. Accordingly, less curing strain may occur by the reduced adhesive 39.

Moreover, the X-ray grid 1 of Embodiment 1 has sufficient strength. That is because the first joining member 15 has a thickness larger at both ends E thereof in the x-direction than the center portion C between the both ends E. The both ends of the absorbing foil strips 10a in the x-direction have to be supported securely for realizing linearity and regular arrangement of the absorbing foil strips 10a. According to the configuration of Embodiment 1, a thick portion of the first joining member 15 supports the both ends of the absorbing foil strips in the x-direction. Consequently, the X-ray grid 1 has enhanced strength.

Moreover, direct X-rays may efficiently pass through the X-ray grid 1 of Embodiment 1. That is because the first joining member 15 has a smaller thickness in the center portion C thereof. When a shadow of the first joining member 15 falls on a fluoroscopic X-ray image of a subject M, visibility in the fluoroscopic X-ray image may be reduced, accordingly. On the other hand, according to the configuration of Embodiment 1, the first joining member 15 has a thickness possibly reduced in the enter portion C thereof. Consequently, the first joining member 15 does not prevent direct X-rays from traveling that fall on the fluoroscopic X-ray image of the subject M.

The X-ray grid 1 of Embodiment 1 has enhanced strength. That is, the first joining member 15 and the second joining member 16 support the absorbing foil strips 10a. Here, the second joining member 16 has a thickness larger at both ends thereof in the x-direction than the first joining member 15 in the center portion C between the both ends E. In other words, the second joining member 16 of Embodiment 1 has the same effect as the first joining member 15.

According to the configuration of Embodiment 1, the gelatinous adhesive 39 is spread with the spatula 40, whereby the adhesive 39 applied on the first seat cover 11 is shaped. Consequently, the first joining member 15 has a uniform thickness at the ends E thereof. That is, according to the configuration of Embodiment 1 the adhesive 39 penetrates through the gaps between the absorbing foil strips 10a by a uniform amount, which result in no variation thereof among the gaps between the absorbing foil strips 10a. Thus, even when the gap D is provided between the first joining member 15 and the second joining member 16, a sufficient amount of the adhesive 39 penetrates the gaps between the absorption foils 10a, which results in the X-ray grid 1 according to Embodiment 1 having enhanced mechanical strength.

According to the configuration of Embodiment 1, even when the absorbing foil strips 10a in the X-ray grid 1 are cut to have an even length in the x-direction in manufacture of the X-ray grid 1, the absorber 10 never yields to be deformed upon cutting of both ends of the absorbing foil strips 10a. That is, the first joining member 15 and the second joining member 16 extend in the gap between the absorbing foil strips 10a adjacent to each other, thereby connecting, the adjacent absorbing foil strips 10a to each other in the y-direction. When the X-ray grid 1 is cut at the both ends thereof to have an even length in such state, no absorbing foil strip 10a is deformed. That is because the absorbing foil strips 10a adjacent to each other are secured with the first joining member 15 and the second joining member 16 in the y-direction.

Embodiment 2

Next, description will be given of X-ray apparatus provided with the X-ray grid 1 described in Embodiment 1 with reference to the drawings.

Figure 18:
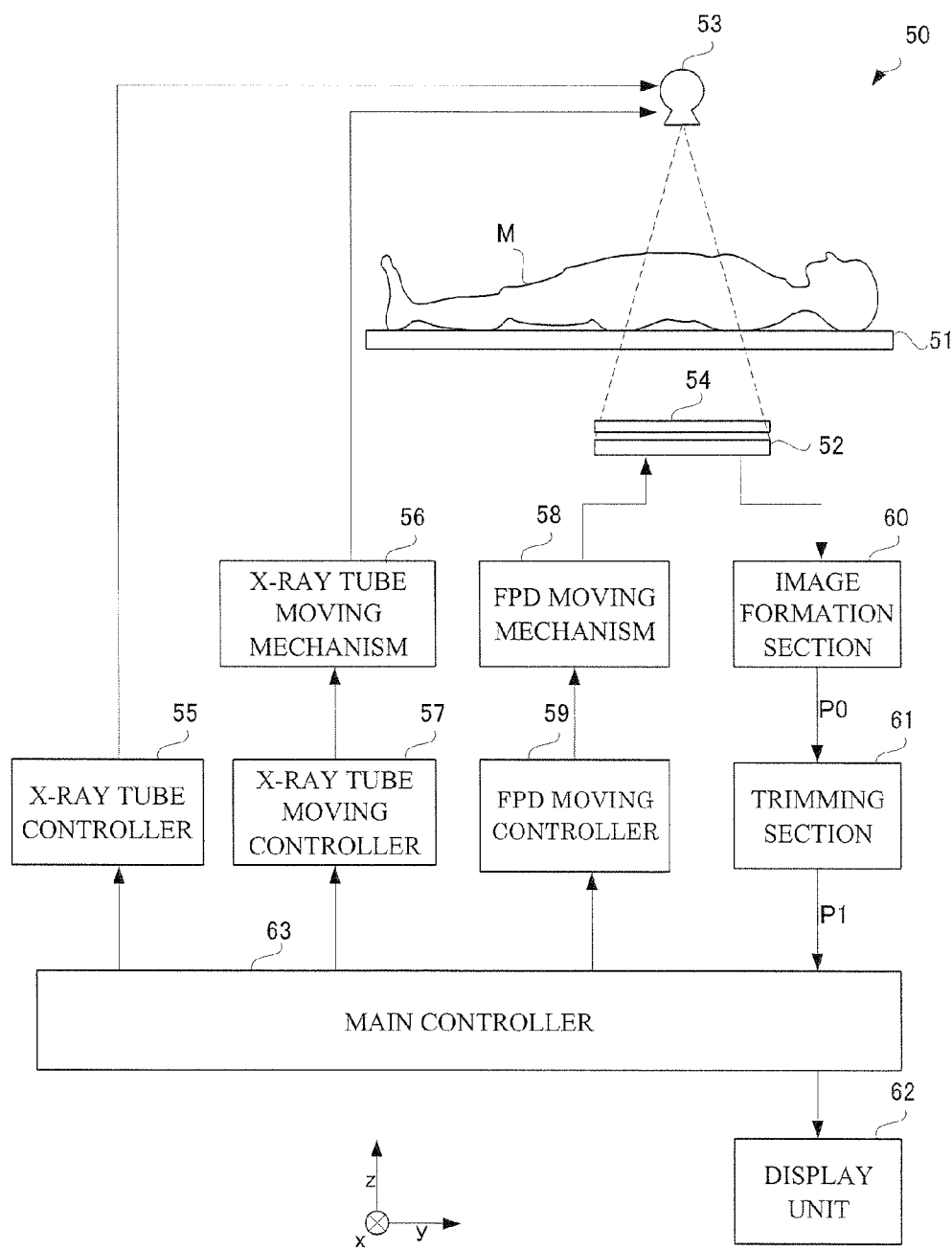
FIG. 18 is a functional block diagram showing a configuration of X-ray apparatus according to Embodiment 2.
Figure 20:
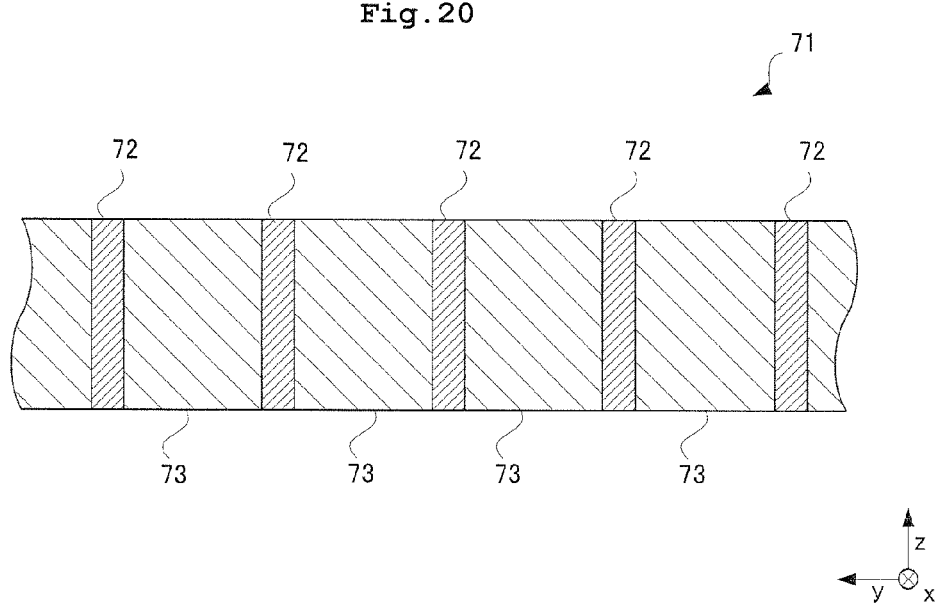
FIG. 20 is a sectional view showing an X-ray grid according to a conventional configuration.
Figure 21:
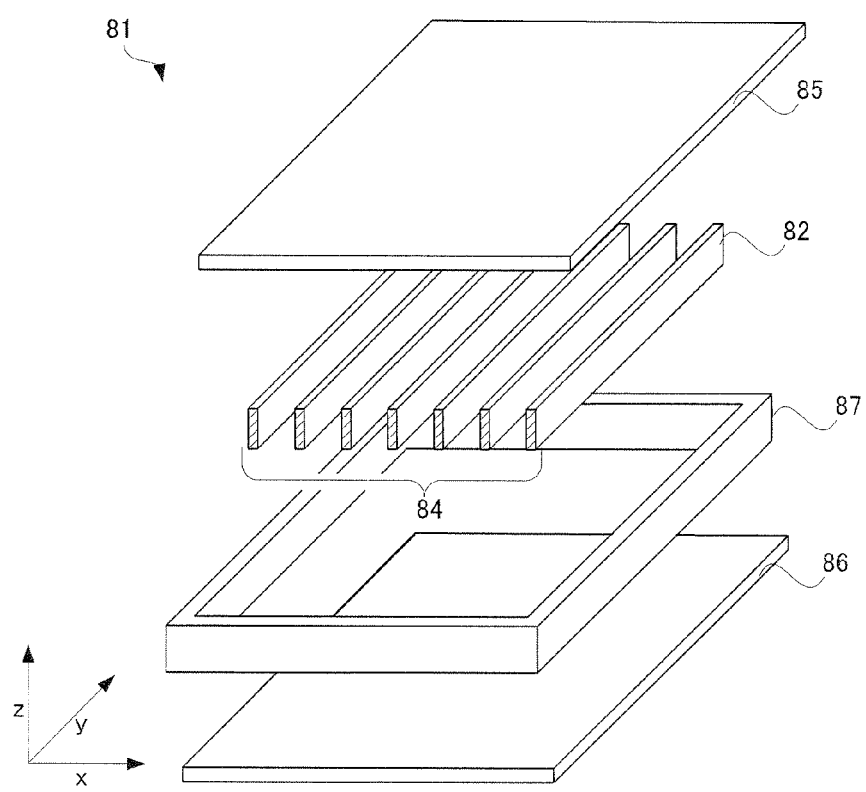
FIG. 21 is an exploded perspective view showing the X-ray grid according to the conventional configuration.

FIG. 18 is a functional block diagram showing a configuration of X-ray apparatus according to Embodiment 2. As shown in FIG. 18, X-ray apparatus 50 according to Embodiment 2 includes a top board 51 for supporting a subject M; an FPD 52 having an image sensor provided below the top board 51; an X-ray tube 53 provided above the top board 51 for irradiating the FPD 52 with X-ray beams in a cone shape; an X-ray grid 54 provided to cover a radiation detecting plane of the FPD 52 for removing scattered X-rays; an X-ray tube controller 55 for controlling a tube voltage in the X-ray tube 53; an X-ray tube moving mechanism 56 for moving the X-ray tube 53, and an X-ray tube moving controller 57 for controlling movement thereof; an FPD moving mechanism 58 for moving the FPD 52, and an FPD moving controller 57 for controlling movement thereof; an image formation section 60 for forming an original image P0 based on signals outputted from the FPD 52; a trimming section 61 for performing a trimming treatment to the original image P0 outputted from the image formation section 60; and a display unit 62 for displaying a fluoroscopic X-ray image P1. Here, the FPD 52 and the X-ray tube 53 correspond to the radiation detecting device and the radiation source respectively, in this invention. The image formation section 60 and the trimming section 61 correspond to the image formation device and the trimming device in this invention in addition, the X-ray grid 54 corresponds to the X-ray grid 1 according to Embodiment 1.

The X-ray apparatus 50 also includes a main controller 63 for performing an overall control of each controller 55, 57, and 59. The main controller 63 has a CPU, and realizes the controllers 55, 57, and 59 as well as the trimming section 61 by executing various programs.

In order to take the fluoroscopic X-ray image P1 with the X-ray apparatus 50 according to Embodiment 2, the subject M firstly lies on the back thereof on the top board 51. Subsequently, the FPD 52 and the X-ray tube 53 move into a position where a site of interest of the subject M is sandwiched. Then, the X-ray tube 53 moves in the z-direction to determine a size of the field of view. The X-ray tube 53 is controlled to apply X-ray beams in a cone shape. Here, X-ray beams in a cone shape are pulsed. In addition, a focus of X-ray beams conforms to the concentrating point where the grooves of the comb plates extend. Accordingly, the absorbing foil strips of the X-ray grid 54 are inclined along a traveling direction of X-rays that constitute X-ray beams in a cone shape.

X-rays transmitting the subject M pass through the X-ray grid 54 into the FPD 52. The FPD 52 sends X-ray detection data into the image formation section 60. The image formation section 60 forms the original image P0 based on this, and sends it to the trimming section 61. The original image P0 also includes data on detected ends of X-ray beams. The ends of X-ray beams pass through the end of the X-ray grid 54. Consequently, the ends of X-ray beams transmit the ends E as the thick portion in the first joining member 15. The trimming section 61 cuts off a given region in the original image P0 where a shadow of the ends E falls to form the fluoroscopic X-ray limp P1.

FIG. 19 is a schematic view showing operations of the X-ray apparatus according to Embodiment 2. The X-ray grid 54 has the ends E at both ends thereof in the x-direction. Accordingly, as shown in FIG. 19(a), the given region in the original P0 extends in two ends L of the original P0 parallel to each other. As shown in FIG. 19(b), the trimming section 61 cuts off the two ends L of the original P0 as the given region, and outputs only a center portion of the original P0. The center portion of the original image P0 is an image of passing through the center portion C of the X-ray grid 54. The first joining member 15 has a smaller thickness in the center portion C thereof, which results in possibly suppressed absorption of X-rays in the center portion C of the first joining member 15. Consequently, the fluoroscopic X-ray image P1 formed with the trimming section 61 is suitable for diagnosis.

Here, the position where the shadow of the thick portion of the second joining member 16 falls on the original image P0 is same as that of the first joining member 15. Thus, the above treatment with the trimming section 61 may simultaneously realize removal of shadows of both ends in the x-direction of the second joining member 16 that falls on the original image P0. The display unit 62 displays a formed fluoroscopic X-ray image P1.

As above, the X-ray apparatus 50 of Embodiment 2 with the X-ray grid of Embodiment 1 may provide a fluoroscopic X-ray image P1 suitable for diagnosis. The trimming section 61 provided in the X-ray apparatus 50 of Embodiment 2 cuts off the given region in the original image P0 where the ends E fall. Accordingly, the fluoroscopic X-ray image P1 has no shadow of both ends in the x-directions of the first joining, member 15 and the second joining member 16, and thus suitable for diagnosis.

This invention is not limited to the foregoing embodiment, but may be modified as follows.

(1) Each foregoing embodiment discusses a medical apparatus. This invention is applicable also to apparatus for industrial use and for the nuclear field.

(2) X-rays used in each foregoing embodiment are an example of radiation in this invention. Therefore, this invention may be adapted also for radiation other than X-rays.

(3) The X-ray grid of each foregoing embodiment has absorbing foil strips arranged in a window blind. The X-ray grid may have absorbing foil strips in a lattice shape to form a cross grid.

INDUSTRIAL UTILITY

As described above, this invention is suitable for radiographic apparatus for medical uses.

The invention claimed is:
1. A radiation grid comprising:
an absorber having strip absorbing foil strips that extend in an extension direction for absorbing radiation arranged in an arrangement direction perpendicular to the extension direction, and having an incident plane where radiation enters and an emitting plane where radiation emits;
a first covering member for covering one plane of the incident plane or the emitting plane of the absorber;
a second covering member for covering the other plane other than the one plane of the absorber;
a first joining member arranged at a contact portion of each absorbing foil strip constituting the absorber and the first covering member for providing integration of both thereof; and
a second joining member arranged at a contact portion of each absorbing foil strip constituting the absorber and the second covering member for providing integration of both thereof,
a gap being provided between the first joining member and the second joining member, and
the first joining member having a thickness larger at both ends thereof in the extension direction than a center portion between the both ends.
2. The radiation grid according to claim 1, wherein
the second joining member has a thickness larger at both ends thereof in the extension direction than the center portion between the both ends.

3. The radiation grid according to claim 2, wherein
at both ends of the first joining member in the extension direction, the first joining member extends in a gap between the absorbing foil strips adjacent to each other for connecting the adjacent absorbing foil strips.
4. The radiation grid according to claim 2, wherein
at both ends of the second joining member in the extension direction, the second joining member extends in a gap between the absorbing foil strips adjacent to each other for connecting the adjacent absorbing foil strips.
5. The radiation grid according to claim 1, wherein
at both ends of the first joining member in the extension direction, the first joining member extends in a gap between the absorbing foil strips adjacent to each other for connecting the adjacent absorbing foil strips.
6. The radiation grid according to claim 5, wherein
at both ends of the second joining member in the extension direction, the second joining member extends in a gap between the absorbing foil strips adjacent to each other for connecting the adjacent absorbing foil strips.
7. The radiation grid according to claim 1, wherein
at both ends of the second joining member in the extension direction, the second joining member extends in a gap between the absorbing foil strips adjacent to each other for connecting the adjacent absorbing foil strips.
8. Radiographic apparatus comprising:
a radiation source for emitting radiation beams;
a radiation detecting device for detecting radiation beams to form detection signals;
a radiation grid arranged so as to cover a radiation detection surface where the radiation detecting device detects radiation;
an image formation device for forming an original image based on the detection signals; and
a trimming device for cutting off a given region in the original image to form a fluoroscopic image,
the given region in the original image being a region where a shadow of both ends in the radiation grid falls,
the radiation grid comprising:
an absorber having strip absorbing foil strips that extend in an extension direction for absorbing radiation arranged in an arrangement direction perpendicular to the extension direction, and having an incident plane where radiation enters and an emitting plane where radiation emits;
a first covering member for covering one plane of the incident plane or the emitting plane of the absorber;
a second covering member for covering the other plane other than the one plane of the absorber;
a first joining member arranged at a contact portion of each absorbing foil strip constituting the absorber and the first covering member for providing integration of both thereof; and
a second joining member arranged at a contact portion of each absorbing foil strip constituting the absorber and the second covering member for providing integration of both thereof,
a gap being provided between the first joining member and the second joining member, and
the first joining member having a thickness larger at both ends thereof in the extension direction than a center portion between the both ends.

* * * * *